United States Patent
Gallet et al.

(10) Patent No.: US 7,001,902 B2
(45) Date of Patent: Feb. 21, 2006

(54) 4-(2 PHENYLTHIAZOL-5-YL)-1, 4-DIAZABICYCLO-[3.2.2]NONANE DERIVATIVES, PREPARATION AND THERAPEUTIC USE THEREOF

(75) Inventors: Thierry Gallet, Palaiseau (FR); Frédéric Galli, Vaucresson (FR); Odile Leclerc, Massy (FR); Alistair Lochead, Charenenton-le-Pont (FR)

(73) Assignee: sanotl-aventis, Paris (FR)

( * ) Notice: Subject to any disclaimer, the term of this patent is extended or adjusted under 35 U.S.C. 154(b) by 428 days.

(21) Appl. No.: 10/276,822

(22) PCT Filed: May 29, 2001

(86) PCT No.: PCT/FR01/01650

§ 371 (c)(1),
(2), (4) Date: Nov. 18, 2002

(87) PCT Pub. No.: WO01/92260

PCT Pub. Date: Dec. 6, 2001

(65) Prior Publication Data

US 2004/0029884 A1  Feb. 12, 2004

(30) Foreign Application Priority Data

May 31, 2000 (FR) .................... 00 06978

(51) Int. Cl.
*A61P 25/00* (2006.01)
*A61K 31/55* (2006.01)
*C07D 471/08* (2006.01)

(52) U.S. Cl. .......... 514/219; 514/221; 540/556

(58) Field of Classification Search ............... 514/219, 514/221; 540/556
See application file for complete search history.

(56) References Cited

U.S. PATENT DOCUMENTS 5,478,939 A   12/1995   Trybulski et al. .......... 544/336
6,407,095 B1   6/2002   Lochead et al. .......... 514/221

FOREIGN PATENT DOCUMENTS

EP   0307140   3/1989
WO   WO 00/34279   6/2000

*Primary Examiner*—Brenda Coleman
(74) *Attorney, Agent, or Firm*—Balaram Grupta

(57) ABSTRACT

Compound corresponding to the general formula (I)

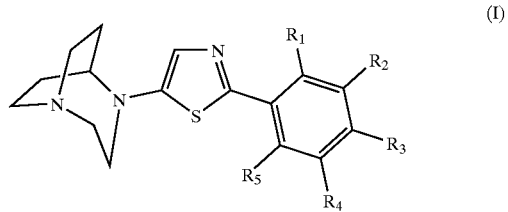

in which $R_1$, $R_2$, $R_3$, $R_4$ and $R_5$ each represent a hydrogen or halogen atom or a nitro, amino, trifluoromethyl, trifluoroalkoxy, cyano, hydroxyl, $(C_1-C_6)$alkyl or $(C_1-C_6)$alkoxy group and $R_6$ represents a $(C_1-C_6)$alkyl group.

Therapeutic application.

4 Claims, No Drawings

4-(2 PHENYLTHIAZOL-5-YL)-1, 4-DIAZABICYCLO-[3.2.2]NONANE DERIVATIVES, PREPARATION AND THERAPEUTIC USE THEREOF

This application is a National Stage entry under 35 U.S.C. §371 of International application No. PCT/FR01/01650 filed May 29, 2001, which is incorporated herein by reference in its entirety.

The compounds of the present invention correspond to the general formula (I)

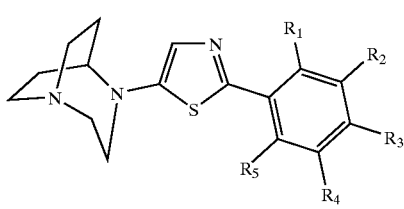

in which $R_1$, $R_2$, $R_3$, $R_4$ and $R_5$ each represent, independently of each other, a hydrogen or halogen atom or a nitro, amino, trifluoromethyl, trifluoroalkoxy, cyano, hydroxyl, ($C_1$–$C_6$) alkyl or ($C_1$–$C_6$)alkoxy group.

The compounds of the invention may exist in the form of bases or of addition salts with acids.

In accordance with the invention, the compounds of general formula (I) may be prepared by reacting 1,4-diazabicyclo[3.2.2]nonane, of formula (II)

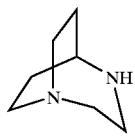

with a compound of general formula (III)

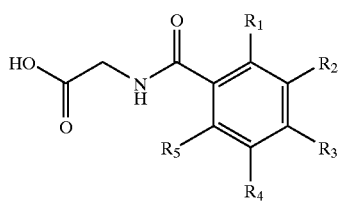

in which $R_1$, $R_2$, $R_3$, $R_4$ and $R_5$ are as defined above, and the above product is then cyclized in the presence of 4-methoxyphenylthionophosphine sulfide dimer (Lawesson's reagent), or alternatively in the presence of 2,4-bis(phenylthio)-1,3,2,4-dithiadiphosphetane 2,4-disulfide (cf. Synth. Commun. 1984, 827).

The preparation of 1,4-diazabicyclo[3.2.2]nonane is described in J. Med. Chem. 1993, 36, 2311–2320.

The compounds of general formula (III) are commercially available or are accessible by methods described in the literature.

The examples that follow illustrate the preparation of a number of compounds according to the invention. The elemental microanalyses and the IR and NMR spectra confirm the structures of the compounds obtained.

The numbers indicated in parentheses in the example titles correspond to those in the first column of table 1 given later.

In the compound names, the hyphen "-" forms part of the word, and the underscore line "_" serves merely to indicate the line-break split; it should be removed if it does not occur at a line break, and should not be replaced either by a normal hyphen or by a space.

EXAMPLE 1

Compound 1

4-(2-Phenylthiazol-5-yl)-1,4-diazabicyclo[3.2.2] nonane hydrobromide 1:2

1.1
N-[2-(1,4-Diazabicyclo[3.2.2]non-4-yl)-2-oxoethyl] benzamide 1.06 9 (5.9 mmol) of N-benzoylglycine (hippuric acid) dissolved in 20 ml of chloroform are placed in a 50 ml round-bottomed flask and 2.9 g (17.9 mmol) of 1,1'-carbonylbis-1H-imidazole are added, and the mixture is then stirred at room temperature for one hour.

0.75 g (5.9 mmol) of 1,4-diazabicyclo[3.2.2]nonane dissolved in 5 ml of chloroform is added and the mixture is stirred for 24 hours.

The solvent is evaporated off under reduced pressure and the residue is purified by chromatography on a column of silica gel, eluting with a 90/10/1 mixture of chloroform, methanol and aqueous ammonia.

1.3 g of product are obtained in the form of an oil.

1.2 4-(2-Phenylthiazol-5-yl)-1,4-diazabicyclo[3.2.2] nonane hydrobromide 1:2

1.3 g (4.5 mmol) of N-[2-(1,4-diazabicyclo[3.2.2]non-4-yl)-2-oxoethyl]benzamide dissolved in 50 ml of toluene are placed in a 100 ml round-bottomed flask, 1.8 9 (4.5 mmol) of 4-methoxyphenylthionophosphine sulfide dimer (Lawesson's reagent) are added and the mixture is heated at 120° C. for 18 hours.

The solvent is evaporated off under reduced pressure and the residue is purified by chromatography on a column of silica gel, eluting with a 95/5/0.5 mixture of chloroform, methanol and aqueous ammonia. The product obtained is dissolved in isopropyl alcohol and a 33% solution of hydrobromic acid in acetic acid is added. The crystals obtained (0.14 g) are collected by filtration.

Melting point: 275–277° C.

EXAMPLE 2

Compound 5

4-[2-(2-Methylphenyl)thiazol-5-yl]-1,4-diazabicyclo [3.2.2]nonane hydrobromide 1:2

2.1 N-[2-(1,4-Diazabicyclo[3.2.2]non-4-yl)-2-oxoethyl]-2-methylbenzamide 0.47 g (2.28 mmol) of dicyclohexylcarbodiimide dissolved in 20 ml of dioxane is placed in a 50 ml round-bottomed flask at room temperature. 0.4 g (2.07 mmol) of N-(o-toluyl)glycine is then added and the mixture is stirred for 30 minutes at room temperature.

0.26 g (2.07 mmol) of 1,4-diazabicyclo[3.2.2]nonane dissolved in 5 ml of dioxane is added and the mixture is stirred for one hour.

50 ml of water are added, the precipitate formed is filtered off and the aqueous phase is extracted with chloroform. The organic phase is extracted with-aqueous 0.1N hydrochloric acid solution and the aqueous phase is basified to pH 10 by addition of concentrated aqueous sodium hydroxide solution and extracted with chloroform.

The organic phase is dried over sodium sulfate and concentrated under reduced pressure. 0.41 g of product is obtained in solid form.

Melting point: 177° C.

2.2 4-[2-(2-Methylphenyl)thiazol-5-yl]-1,4-diazabicyclo[3.2.2]nonane hydrobromide 1:2

0.41 g (1.36 mmol) of N-[2-(1,4-diazabicyclo[3.2.2]non-4-yl)-2-oxoethyl]-2-methylbenzamide suspended in 20 ml of xylene is placed in a 50 ml round-bottomed flask, 0.611 g (1.5 mmol) of 2,4-bis(phenylthio)-1,3,2,4-dithiadiphosphetane 2,4-disulfide is added and the mixture is refluxed for 20 hours.

The solvent is evaporated off under reduced pressure and the residue is purified by chromatography on a column of silica gel, eluting with a 95/5/0.5 mixture of chloroform, methanol and aqueous ammonia.

The product obtained is dissolved in ethanol, a 33% solution of hydrobromic acid in acetic acid is added and the crystals obtained are recrystallized from isopropyl alcohol.

0.168 g of product is obtained in solid form.

Melting point: 276–279° C.

EXAMPLE 3

Compound 7

4-[2-(3-Methoxyphenyl)thiazol-5-yl]-1,4-diazabicyclo[3.2.2]nonane oxalate 1:1

3.1 N-(3-Methoxybenzoyl)glycine 1.5 g (20 mmol) of glycine dissolved in 20 ml of aqueous 2N sodium hydroxide solution are placed in a 50 ml round-bottomed flask, the medium is heated to 50° C., 3.1 ml (20 mmol) of 3-methoxybenzoyl chloride are added dropwise and the mixture is stirred at 50° C. for 30 minutes. It is cooled to room temperature and kept stirring for 20 hours.

The reaction medium is cooled to 4° C. and 2 ml of concentrated aqueous hydrochloric acid solution are added slowly. The precipitate obtained is collected by filtration and recrystallized from toluene.

2.77 g of crystals are obtained.

Melting point: 124° C.

3.2 N-[2-(1,4-Diazabicyclo[3.2.2]non-4-yl)-2-oxoethyl]-3-methoxybenzamide 0.42 g (2 mmol) of N-(3-methoxybenzoyl)glycine dissolved in 20 ml of dioxane is placed in a 50 ml round-bottomed flask, 0.45 g (2.2 mmol) of dicyclohexylcarbodiimide is added and the mixture is stirred at room temperature for 30 minutes, 0.25 g (2 mmol) of 1,4-diazabicyclo[3.2.2]nonane is added and the mixture is stirred for a further two hours.

20 ml of water are added, the precipitate formed is filtered off and the filtrate is extracted with chloroform. The organic phase is extracted with aqueous 0.1N hydrochloric acid solution and the aqueous extraction phase is basified to pH 10 by addition of concentrated aqueous sodium hydroxide solution and extracted with chloroform. The organic phase is dried over sodium sulfate-and concentrated under reduced pressure.

0.43 g of product is obtained in the form of an amorphous solid.

3.3 4-[2-(3-Methoxyphenyl)thiazol-5-yl]-1,4-diazabicyclo[3.2.2]nonane oxalate 1:1

0.42 g (1.32 mmol) of N-[2-(1,4-diazabicyclo[3.2.2]non-4-yl)-2-oxoethyl]-3-methoxybenzamide suspended in 15 ml of xylene is placed in a 25 ml round-bottomed flask, 0.59 g (1.45 mmol) of 2,4-bis(phenylthio)-1,3,2,4-dithiadiphosphetane 2,4-disulfide is added and the mixture is refluxed for 20 hours.

Aqueous 0.5N sodium hydroxide solution is added and the aqueous phase is extracted with chloroform. The organic phase is dried over sodium sulfate and evaporated under reduced pressure, and the residue is purified by chromatography on a column of silica gel, eluting with a 90/10 mixture of ethyl acetate and methanol. The product obtained is dissolved in acetone, a solution of oxalic acid in acetone is added and the crystals obtained (0.166 g) are collected by filtration.

Melting point: 192–193° C.

EXAMPLE 4

Compound 6

4-[2-(4-Methoxyphenyl)thiazol-5-yl]-1,4-diazabicyclo[3.2.2]nonane oxalate 1:1

4.1 N-(4-Methoxybenzoyl)glycine 2.93 g (39 mmol) of glycine dissolved in 41 ml of aqueous 1N sodium hydroxide solution are placed in a 250 ml round-bottomed flask, the mixture is cooled to 4° C., 41 ml of aqueous 1N sodium hydroxide solution and a solution of 7 g (0.041 mol) of 4-methoxybenzoyl chloride in 10 ml of dioxane are added simultaneously, dropwise over 45 minutes, and the mixture is stirred for 20 hours.

Concentrated aqueous hydrochloric acid solution is added to pH 1 and the precipitate formed is collected by filtration and recrystallized from isopropyl alcohol.

3.74 g of product are obtained.

Melting point: 173° C.

4.2 N-[2-(1,4-Diazabicyclo[3.2.2]non-4-yl)-2-oxoethyl]-4-methoxybenzamide 0.42 g (2 mmol) of N-(4-methoxybenzoyl)glycine dissolved in 20 ml of dioxane is placed in a 50 ml round-bottomed flask, 0.45 g (2.2 mmol) of dicyclohexylcarbodiimide is added, the mixture is stirred at room temperature for 30 minutes, 0.25 g (2 mmol) of 1,4-diazabicyclo[3.2.2] nonane is added and the mixture is stirred for a further one hour. 20 ml of water are added, the precipitate formed is filtered off, the filtrate is extracted with chloroform, the organic phase is extracted with aqueous 0.1N hydrochloric acid solution and the aqueous extraction phase is basified to pH 10 by addition of concentrated aqueous sodium hydroxide solution and extracted with chloroform. The organic phase is dried over sodium sulfate and concentrated under reduced pressure.

0.49 g of product is obtained in the form of an amorphous solid.

4.3 4-[2-(4-Methoxyphenyl)thiazol-5-yl]-1,4-diazabicyclo[3.2.2]nonane oxalate 1:1

0.47 g (1.48 mmol) of N-[2-(1,4-diazabicyclo[3.2.2]non-4-yl)-2-oxoethyl]-4-methoxybenzamide dissolved in 15 ml of xylene is placed in a 25 ml round-bottomed flask, 0.66 g (1.63 mmol) of 2,4-bis(phenylthio)-1,3,2,4-dithiadiphosphetane 2,4-disulfide is added and the mixture is refluxed for two hours.

The solvent is evaporated off under reduced pressure and the residue is purified by chromatography on a column of silica gel, eluting with a 95/5/0.5 mixture of ethyl acetate, methanol and diethylamine. The product obtained is dissolved in ethanol and a solution of oxalic acid in ethanol is added. The crystals obtained (0.176 g) are collected by filtration.

Melting point: 219–222° C.

EXAMPLE 5

Compound 8

4-[2-(3-Bromophenyl)thiazol-5-yl]-1,4-diazabicyclo[3.2.2]nonane oxalate 1:1

5.1 N-(3-Bromobenzoyl)glycine 1.5 g (20 mmol) of glycine dissolved in 20 ml of aqueous 2N sodium hydroxide solution are placed in a 50 ml round-bottomed flask. The medium is heated to 50° C., 2.6 ml (20 mmol) of 3-bromobenzoyl chloride are added dropwise, and the mixture is stirred for 30 minutes at this temperature, cooled to room temperature and stirred for 20 hours.

The reaction medium is cooled to 4° C., 2 ml of concentrated aqueous hydrochloric acid solution are added slowly and the precipitate obtained is collected by filtration and recrystallized from toluene.

3.21 g of crystals are obtained.

5.2 N-[2-(1,4-Diazabicyclo[3.2.2]non-4-yl)-2-oxoethyl]-3-bromobenzamide 0.77 g (3 mmol) of N-(3-bromobenzoyl)glycine dissolved in 30 ml of dioxane is placed in a 100 ml round-bottomed flask, 0.68 g (3.3 mmol) of dicyclohexylcarbodiimide is added and the mixture is stirred at room temperature for 30 minutes, 0.38 g (3 mmol) of 1,4-diazabicyclo[3.2.2]nonane is added and the mixture is stirred for a further two hours. 30 ml of water are added and the precipitate formed is filtered off, the filtrate is extracted with chloroform and the organic phase is then extracted with aqueous 0.1N hydrochloric acid solution. The aqueous extraction phase is basified to pH 10 by addition of concentrated aqueous sodium hydroxide solution and extracted with chloroform. The organic phase is dried over sodium sulfate and concentrated under reduced pressure.

0.95 g of product is obtained in the form of an oil.

5.3 4-[2-(3-Bromophenyl)thiazol-5-yl]-1,4-diazabicyclo[3.2.2]nonane oxalate 1:1

0.93 g (2.54 mmol) of N-[2-(1,4-diazabicyclo[3.2.2]non-4-yl)-2-oxoethyl]-3-bromobenzamide dissolved in 25 ml of xylene is placed in a 25 ml round-bottomed flask, 1.14 g (2.79 mmol) of 2,4-bis(phenylthio)-1,3,2,4-dithiadiphosphetane 2,4-disulfide are added and the mixture is refluxed for two hours.

The solvent is evaporated off under reduced pressure and the residue is purified by chromatography on a column of silica gel, eluting with a 95/5/0.5 mixture of ethyl acetate, methanol and aqueous ammonia. The product obtained is dissolved in ethanol and a solution of oxalic acid in ethanol is added. The crystals obtained (0.055 g) are collected by filtration.

Melting point: 161–163° C.

Table 1 below illustrates the chemical structures and physical properties of a number of compounds of the invention.

TABLE

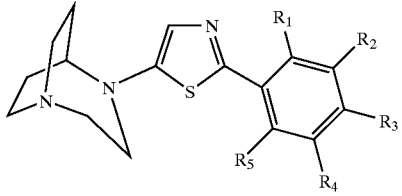

(I)

| No. | $R_1$ | $R_2$ | $R_3$ | $R_4$ | $R_5$ | Salt | m.p. (° C.) |
|---|---|---|---|---|---|---|---|
| 1 | H | H | H | H | H | HBr 2:1 | 275–277 |
| 2 | H | H | $CH_3$ | H | H | HBr 1:1 | 287–290 |
| 3 | H | $CH_3$ | H | H | H | HBr 1:1 | 272–274 |
| 4 | H | H | $NO_2$ | H | H | HBr 1:1 | 309–313 |
| 5 | $CH_3$ | H | H | H | H | HBr 2:1 | 276–279 |
| 6 | H | H | $OCH_3$ | H | H | ox. 1:1 | 219–222 |
| 7 | H | $OCH_3$ | H | H | H | ox. 1:1 | 192–193 |
| 8 | H | Br | H | H | H | ox. 1:1 | 161–163 |
| 9 | F | H | H | F | H | ox. 1:1 | 217–219 |
| 10 | H | H | $CF_3$ | H | H | ox. 1:1 | 214–217 |
| 11 | I | H | H | H | H | ox. 1:1 | 214–217 |
| 12 | H | H | $OCF_3$ | H | H | ox. 1:1 | 153–155 |
| 13 | H | H | Br | H | H | ox. 1:1 | 214–215 |
| 14 | H | $OCH_3$ | $OCH_3$ | H | H | ox. 1:1 | 196–198 |
| 15 | H | F | F | H | H | ox. 1:1 | 188–190 |
| 16 | Cl | Cl | H | H | H | ox. 1:1 | 189–191 |
| 17 | H | Cl | H | Cl | H | ox. 1:1 | 224–226 |
| 18 | H | $OCH_3$ | H | $OCH_3$ | H | ox. 1:1 | 180–181 |
| 19 | OH | H | H | H | H | ox. 1:1 | 196–197 |
| 20 | Br | H | H | H | H | ox. 1:1 | 193–194 |

Key
In the "Salt" column, "HBr" denotes a hydrobromide and "ox." denotes an oxalate. The acid:base molar ratio is indicated opposite.

The compounds of the invention underwent tests that demonstrated their value as therapeutic substances.

Thus, they were studied as regards their affinity with respect to nicotinic receptors containing the α7 subunit, according to the methods described by Marks and Collins, *Pharmacol.* 1982, 22, 554 and Marks et al., *Mol. Pharmacol.* 1986, 30, 427.

Male OFA rats weighing 150 to 200 g are decapitated, the entire brain is removed quickly and homogenized using a Polytron™ mill in 15 volumes of a 0.32 M sucrose solution at 4° C., followed by centrifugation at 1000×g for 10 minutes. The pellet is discarded and the supernatant is centrifuged at 8000×g for 20 minutes at 4° C. The pellet is recovered and homogenized using a Polytron™ mill in 15 volumes of double-distilled water at 4° C., followed by centrifugation at 8000×g for 20 minutes. The pellet is discarded and the supernatant and the buffy coat are centrifuged at 40 000×g for 20 minutes. The pellet is recovered, resuspended in 15 volumes of double-distilled water at 4° C. and centrifuged again at 40 000×g for 20 minutes, before being stored at −80° C.

On the day of the experiment, the tissue is thawed slowly and suspended in 5 volumes of buffer. 150 µl of this membrane suspension are preincubated at 37° C. for 30 minutes, in the dark, in the presence or absence of the test compound. Next, the membranes are incubated for 60 minutes at 37° C., in the dark, in the presence of 50 µl of 1 nM [$^3$H]α-bungarotoxin in a final volume of 250 µl of 20 mM HEPES buffer. The reaction is stopped by filtration through Whatman GF/C™ filters pretreated for 3 hours with 0.05% polyethyleneimine. The filters are rinsed with 2×5 ml of buffer at 4° C. and the radioactivity retained on each filter is measured by liquid scintigraphy. The nonspecific binding in the presence of α-bungarotoxin at 1 µM is determined; the nonspecific binding represents about 60% of the total binding recovered on the filter. For each concentration of test compound, the percentage of inhibition of the specific binding of [$^3$H] α-bungarotoxin is determined, followed by calculation of the $IC_{50}$ value, which is the concentration of compound that inhibits the specific binding by 50%.

The $IC_{50}$ values for the purest compounds of the invention are between 0.020 and 0.500 µM.

The compounds of the invention were also studied as regards their affinity with respect to nicotinic receptors containing the $\alpha_4\beta_2$ subunit, according to the methods described by Anderson and Arnericin *Eur. J. Pharmacol.* 1994, 253, 261 and by Hall et al. in *Brain Res.* 1993, 600, 127.

Male Sprague-Dawley rats weighing 150 to 200 g are decapitated, the entire brain is removed quickly and homogenized in 15 volumes of a 0.32 M sucrose solution at 4° C., followed by centrifugation at 1000×g for 10 minutes. The pellet is discarded and the supernatant is centrifuged at 20 000×g for 20 minutes at 4° C. The pellet is recovered and homogenized using a Polytron™ mill in 15 volumes of double-distilled water at 4° C., followed by centrifugation at 8000×g for 20 minutes. The pellet is discarded and the supernatant and the buffy coat are centrifuged at 40 300×g for 20 minutes. The pellet is recovered, resuspended in 15 ml of double-distilled water and centrifuged again at 40 000×g, before being stored at −80° C.

On the day of the experiment, the tissue is thawed slowly and suspended in 3 volumes of buffer. 150 µl of this membrane suspension are incubated at 4° C. for 120 minutes in the presence of 100 µl of [3H]-cytisine at 1 nM in a final volume of 500 µl of buffer, in the presence or absence of the test compound. The reaction is stopped by filtration through Whatman GF/B™ filters pretreated with polyethyleneimine. The filters are rinsed with 2×5 ml of buffer at 4° C. and the radioactivity retained on the filter is measured by liquid scintigraphy. The nonspecific binding in the presence of (−)-nicotine at 10 µM is determined; the nonspecific binding represents 75% to 85% of the total binding recovered on the filter. For each concentration of test compound, the percentage of inhibition of the specific binding of $^3$H]-cytisine is determined, followed by calculation of the $IC_{50}$ value, which is the concentration of compound that inhibits the specific binding by 50%.

The $IC_{50}$ values for the purest compounds of the invention are between 1.4 and 4 µM.

The preceding results show that the compounds of the invention are selective ligands for the $\alpha_7$ subunits relative to the $\alpha_4\beta_2$ subunits of the nicotinic receptor.

The results of the various tests suggest the use of the compounds in the treatment or prevention of disorders associated with a dysfunction of the nicotinic receptors, in particular on the central nervous system.

These disorders comprise cognitive impairment, more specifically memory impairment, but also attention impairment, associated with Alzheimer's disease, pathological ageing (Age Associated Memory Impairment, AAMI), Parkinsonian syndrome, trisomy 21 (Down's syndrome), Korsakoff's alcoholic syndrome and vascular dementia (multi-infarct dementia, MID).

The compounds of the invention may also be useful in the treatment of the motor disorders observed in Parkinson's disease or other neurological diseases such as Huntington's chorea, Tourette's syndrome, tardive dyskinesia and hyperkinesia.

The compounds of the invention can also constitute a curative or symptomatic treatment for cerebrovascular accidents and cerebral hypoxic episodes. They can be used in psychiatric pathologies: schizophrenia, depression, anxiety, panic attacks, compulsive and obsessive behavior.

They can prevent the symptoms due to withdrawal from tobacco, from alcohol and from various substances that induce dependence, such as cocaine, LSD, cannabis and benzodiazepines.

Accordingly, a subject of the present invention is also pharmaceutical compositions containing an effective dose of at least one compound according to the invention, in the form of the base or of a pharmaceutically acceptable salt or solvate thereof, and as a mixture, where appropriate, with suitable excipients.

Said excipients are chosen according to the pharmaceutical form and the desired route of administration.

The pharmaceutical compositions according to the invention may thus be intended for oral, sublingual, subcutaneous, intramuscular, intravenous, topical, intratracheal, intranasal, transdermal, rectal or intraocular administration.

The unit forms of administration may be, for example, tablets, gel capsules, granules, powders, oral or injectable solutions or suspensions, transdermal patches or suppositories. Ointments, lotions, and eye lotions may be envisaged for topical administration.

Said unit forms are dosed to allow a daily administration of from 0.01 to 20 mg of active principle per kg of body weight, according to the presentation form.

In order;to prepare tablets, a pharmaceutical vehicle which may be composed of diluents such as, for example, lactose, microcrystalline cellulose or starch and formulation adjuvants, for instance binders (polyvinylpyrrolidone, hydroxypropylmethylcellulose, etc.), glidants, for instance silica, lubricants, for instance magnesium stearate, stearic acid, glyceryl tribehenate or sodium stearylfumarate, is added to the active principle, which may or may not be micronized. Wetting agents or surfactants such as sodium lauryl sulfate may also be added.

The preparation techniques may be direct tabletting, dry granulation, wet granulation or hot melting.

The tablets may be plain, coated, for example with sucrose, or coated with various polymers or other suitable materials. They may be designed to allow a rapid, delayed or sustained release of the active principle by means of polymer matrices or specific polymers used in the coating.

In order to prepare gel capsules, the active principle is mixed with dry pharmaceutical vehicles (simple mixing, dry or wet granulation, or hot melting) or liquid or semi-solid pharmaceutical vehicles.

The gel capsules may be hard or soft, and uncoated or film-coated, so as to have rapid, sustained or delayed activity (for example for an enteric form).

A composition in the form of a syrup or elixir for administration in the form of drops may contain the active principle together with a sweetener, preferably a calorie-free sweetener, methylparaben or propylparaben as antiseptic, a flavor enhancer and a colorant.

The water-dispersible powders and granules may contain the active principle mixed with dispersants or wetting agents, or dispersants such as polyvinylpyrrolidone, and also with sweeteners and flavor enhancers.

For rectal administration, use is made of suppositories prepared with binders that melt at the rectal temperature, for example cocoa butter or polyethylene glycols.

For parenteral administration, aqueous suspensions, isotonic saline solutions or injectable sterile solutions containing pharmacologically compatible dispersants and/or wetting agents, for example propylene glycol or butylene glycol, are used.

The active principle may also be formulated in the form of microcapsules, optionally with one or more supports or additives, or with a polymer matrix or with a cyclodextrin (transdermal patches, sustained-release forms).

The topical compositions according to the invention comprise a medium that is compatible with the skin. They may be especially in the form of aqueous, alcoholic or aqueous-alcoholic solutions, gels, water-in-oil or oil-in-water emulsions having the appearance of a cream or a gel, microemulsions or aerosols, or alternatively in the form of vesicular dispersions containing ionic and/or nonionic lipids. These presentation forms are prepared according to the usual methods of the fields under consideration.

Finally, the pharmaceutical compositions according to the invention may contain, along with a compound of general formula (I), other active principles that may be useful in the treatment of the disorders and diseases indicated above.

The invention claimed is:

1. A compound of the general formula (I)

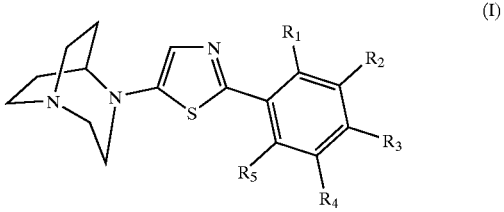

(I)

in which $R_1$, $R_2$, $R_3$, $R_4$ and $R_5$ each represent, independently of each other, a hydrogen or halogen atom or a nitro, amino, trifluoromethyl, trifluoroalkoxy, cyano, hydroxyl, $(C_1-C_6)$alkyl or $(C_1-C_6)$alkoxy group, in the form of the base or of an addition salt with an acid.

2. A process for preparing a compound according to claim 1 wherein 1,4-diazabicyclo[3.2.2]nonane is reacted with a compound of formula (III)

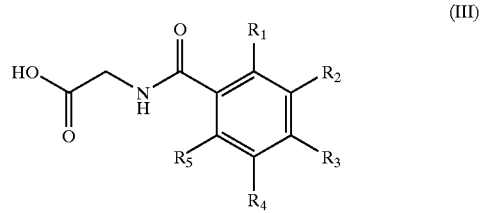

(III)

in which $R_1$, $R_2$, $R_3$, $R_4$ and $R_5$ are as defined in claim 1, and the above product is then cyclyzed in the presence of 4-methoxyphenylthionophosphine sulfide dimer (Lawesson's reagent), or alternatively in the presence of 2,4-bis(phenylthio)-1,3,2,4-dithiadiphosphetane 2,4-disulfide.

3. A method for the treatment of a disease selected from the group consisting of schizophrenia, Alzheimer's disease, Parkinson's disease, Down's syndrome, Korsakoff's alcoholic syndrome, vascular dementia, depression, anxiety, panic attack and obsessive-compulsive behavior, which comprises administering to a patient in need of such treatment an effective amount of a compound according to claim 1.

4. A pharmaceutical composition comprising a compound according to claim 1, combined with an excipient.

* * * * *

UNITED STATES PATENT AND TRADEMARK OFFICE
CERTIFICATE OF CORRECTION

PATENT NO. : 7,001,902 B2  Page 1 of 1
APPLICATION NO. : 10/276822
DATED : February 21, 2006
INVENTOR(S) : Thierry Gallet et al.

It is certified that error appears in the above-identified patent and that said Letters Patent is hereby corrected as shown below:

Title page, right column, item 74, Attorney, Agent, or Firm reads:

"Balaram Grupta"

and should read as:

--Balaram Gupta--

Signed and Sealed this

Fifth Day of September, 2006

JON W. DUDAS
*Director of the United States Patent and Trademark Office*